(12) United States Patent
Kollert et al.

(10) Patent No.: US 9,366,679 B2
(45) Date of Patent: Jun. 14, 2016

(54) METHOD FOR DIAGNOSIS OF PULMONARY INVOLVEMENT IN SYSTEMIC SCLEROSIS

(71) Applicant: Universitaetsklinikum Freiburg, Freiburg (DE)

(72) Inventors: Florian Kollert, Endingen am Kaiserstuhl (DE); Anja Saalbach, Schkeuditz (DE)

(73) Assignee: Universitaetsklinikum Freiburg, Freiburg (DE)

( * ) Notice: Subject to any disclaimer, the term of this patent is extended or adjusted under 35 U.S.C. 154(b) by 0 days.

(21) Appl. No.: 14/390,562

(22) PCT Filed: Mar. 28, 2013

(86) PCT No.: PCT/EP2013/056641
§ 371 (c)(1),
(2) Date: Oct. 3, 2014

(87) PCT Pub. No.: WO2013/149927
PCT Pub. Date: Oct. 10, 2013

(65) Prior Publication Data
US 2015/0093763 A1 Apr. 2, 2015

(30) Foreign Application Priority Data
Apr. 3, 2012 (EP) .................................. 12162923

(51) Int. Cl.
*G01N 33/00* (2006.01)
*G01N 33/68* (2006.01)
*G01N 33/564* (2006.01)

(52) U.S. Cl.
CPC .......... *G01N 33/6872* (2013.01); *G01N 33/564* (2013.01); *G01N 33/6893* (2013.01); *G01N 2333/70503* (2013.01); *G01N 2333/70596* (2013.01); *G01N 2800/10* (2013.01); *G01N 2800/12* (2013.01); *G01N 2800/20* (2013.01); *G01N 2800/321* (2013.01); *G01N 2800/52* (2013.01)

(58) Field of Classification Search
None
See application file for complete search history.

(56) References Cited

U.S. PATENT DOCUMENTS 5,420,016 A * 5/1995 Boguslaski et al. ............ 435/12

OTHER PUBLICATIONS

True et al., CD90/THY1 is overexpressed in prostate cancer-associated fibroblasts and could serve as a cancer biomarker, Modern Pathology, 2010, 23, pp. 1346-1356.*
Barst et al., Treatment of Pulmonary Arterial Hypertension With the Selective Endothelin-A Receptor antagonist Sitaxsentan, Journal of the American College of Cardiology, vol. 47, No. 10, 2006, pp. 2049-2056.*
Barnett et al., Sildenafil in the treatmet of pulmonary hypertension, Vascular Health and Risk Management, 2006:2(4), pp. 411-422.*
Castro, Susan et al., *Biomarkers in Medicine*, vol. 4, No. 1, pp. 133-147 (Feb. 2010).
Hagood, James et al., *The American Journal of Pathology*, vol. 167, No. 2, pp. 365-379 (Aug. 2005).
Hummers, Laura K., *Current Rheumatology Reports*, vol. 12, No. 1, pp. 34-39 (Feb. 1, 2010).
Kollert, Florian et al., *Arthritis Care & Research*, vol. 65, No. 2, pp. 281-287 (Feb. 1, 2013).
Prasse, Antje et al., *Arthritis and Rheumatism*, vol. 56, No. 5, pp. 1685-1693 (May 1, 2007).
Saalbach, A. et al., *Cell and Tissue Research*, vol. 298, No. 2, pp. 307-315 (Nov. 1, 1999).

* cited by examiner

*Primary Examiner* — Gary W Counts
(74) *Attorney, Agent, or Firm* — Chalin A. Smith; Smith Patent

(57) ABSTRACT

A method for the diagnosis and/or therapy control of systemic sclerosis is disclosed wherein soluble CD90 is detected in body fluids. By measuring the concentration of soluble CD90 certain forms of diseases can be differentiated by applying the ex vivo method.

10 Claims, 3 Drawing Sheets

METHOD FOR DIAGNOSIS OF PULMONARY INVOLVEMENT IN SYSTEMIC SCLEROSIS

PRIORITY

This application corresponds to the national phase of International Application No. PCT/EP2013/056641, filed Mar. 28, 2013, which, in turn, claims priority to European Patent Application No. 12.162923.2 filed Apr. 3, 2012, both of which are incorporated by reference herein in their entirety.

BACKGROUND OF THE INVENTION

Systemic Sclerosis (SSc) is a multisystemic fibrotic disease of unknown aetiology. The mortality is high and mostly due to pulmonary involvement. Pathogenic concepts are dealing with endothelial dysfunction and activation, fibroblast abnormalities and alternatively activated macrophages. There are several efforts in establishing markers of pulmonary disease activity in SSc, since mortality is mainly determined by pulmonary arterial hypertension (PAH) and pulmonary fibrosis.

In the skin, systemic sclerosis causes hardening and scarring. The skin may appear tight, reddish or scaly. Blood vessels may also be more visible. SSc can cause pulmonary and other complications. Patients with larger amounts of cutaneous involvement (diffuse SSc) are more likely to have involvement of internal organs.

The joint symptoms that patients with scleroderma have are typically non specific joint pains, which can lead to arthritis, or cause discomfort in tendons or muscles. Joint mobility, especially of the small joints of the hand, may be restricted by calcinosis or skin thickening. Patients may develop muscle weakness, or myopathy.

Some impairment in lung function is almost universally seen in patients with SSc on pulmonary function testing; however, it does not necessarily cause symptoms, such as shortness of breath or cough. Some patients can develop pulmonary hypertension, or elevation in the pressures of the pulmonary arteries. This can be progressive, and lead to right sided heart failure. The earliest manifestation of this may be a decreased diffusion capacity on pulmonary function testing.

Other pulmonary complications in more advanced disease include aspiration pneumonia, pulmonary hemorrhage and pneumothorax. Pulmonary hypertension may be treated with epoprostenol, bosentan and possibly aerolized iloprost.

It is important to determine in patients with SSc risk factors for death. According to Tyndall et al. (Ann. Rheum. Dis., 2010, pp 1809-1815) of the SSc-related death, 35% were attributed to pulmonary fibrosis, 26% to pulmonary arterial hypertension (PAH) and 26% to cardiac causes.

Pulmonary arterial hypertension (PAH) is a serious complication of SSc which is the major cause for death in SSc patients. Since PAH can be treated with suitable medicamentation it is an object to provide a method for diagnosing PAH in vitro. The diagnosis of PAH is difficult since catherization of the heart is a very invasive diagnostic method which indication should be seriously evaluated.

The estimation of the likelihood for underlying PAH in SSc is difficult. For routine diagnostic methods it is possible to measure the content of brain natriuretic peptide (BNP). The more pressure occurs within the heart the higher the BNP value is. BNP values increase only when the stress of the heart is increased. BNP is, however, not specific since the value is elevated also in other heart diseases.

It is an important aspect of the present invention that pulmonary arterial hypertension (PAH) can be reliably detected by the method in vitro disclosed in the present application. The present invention provides a suitable in vitro method which can be easily performed and allows an early and reliable diagnosis on the basis of the concentration of soluble CD90.

SUMMARY OF THE INVENTION

The present invention provides a method for the diagnosis and/or the therapy control of SSc, whereby concentrations of soluble CD90 (sCD90) are detected and measured ex vivo in body fluids of patients. In a preferred embodiment of the present invention the test is performed in an immunological test whereby antibodies bind to the sCD90 molecule. Preferred embodiments of the immunological test are ELISA test, Western blots or line tests. It is also possible to use the test in an automatic test system where a variety of parameters is tested. In such tests suitable antibodies are frequently coated on solid support such as e.g. beads made from polymeric (e.g. polystyrene) or magnetic material. Diagnostic test kits comprising the means for performing the method are also disclosed.

DETAILED DESCRIPTION OF THE PREFERRED EMBODIMENTS

Figure 1:
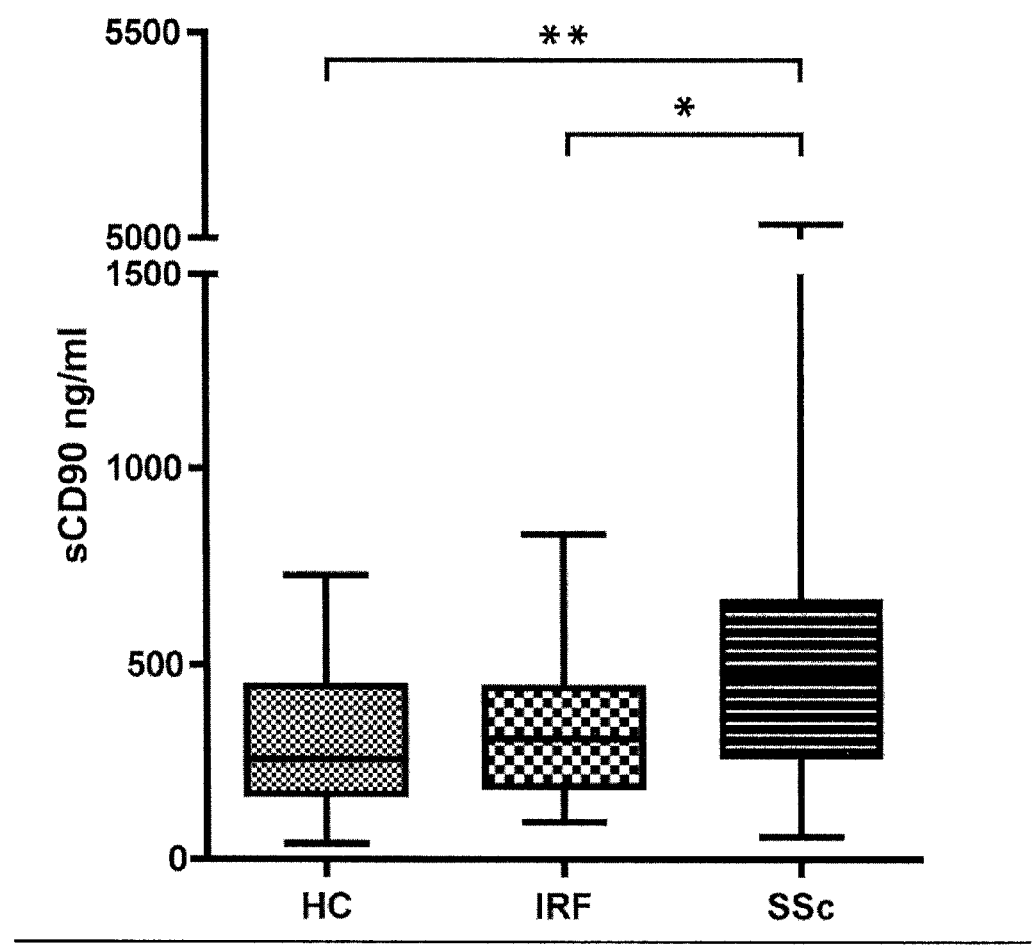
FIG. 1. Soluble CD90 serum concentrations are shown in ng/ml of patients with systemic sclerosis (SSc) compared to healthy control subjects (HC) and patients with idiopathic retroperitoneal fibrosis (IRF). **=p<0.005; *=p<0.05

Human CD90 is a glycosylphosphatidylinisotol (GPI)-anchored adhesion molecule, which is expressed on activated endothelial cells (EC's), fibroblasts, neurons, and a subpopulation of haematopoietic stem cells. Shedding of CD90 from the cell surface of fibroblasts is associated with differentiation towards a profibrogenic myofibroblast phenotype. Saalbach et al. [Cell Tissue Res. (1999), pp. 307-315] describe an enzyme-linked-immunosorbant-assay (ELISA) for detection of sCD90. The patients tested in this publication were, however, not precisely characterized. True et al. (Modern Pathology, 2010, p. 1346-1356) describe that CD90 is overexpressed in prostate cancer associated fibroblast. It is suggested to use CD90 as marker for prostate cancer by performing a urine test.

From the prior art it is not known whether sCD90 serum concentrations are elevated in patients with SSc and whether there is an association with vascular and parenchymal involvement of the lung.

The antigen to be used in the method of the present invention is the soluble CD90 molecule. It is important to select for the immunological test epitopes which occur on CD90 molecules in order to increase the specificity of the test. Furthermore, the epitope which is selected for the test should be one which is well accessible to the antibodies in order to increase the sensitivity of the test method. Another important aspect is that the epitope should not show undesired crossreactivities with other unspecific epitopes which may result in false positive reactions.

In a preferred embodiment of the present invention the CD90 antigen is recombinantly produced, preferably in eukaryotic cells like in insect cells, in particular in *drosophila* cell lines or in CHO (Chinese hamster ovary) cell lines.

In one particularly preferred embodiment the method is performed with a sandwich type ELISA. In the preferred test kit a monoclonal antibody directed to a specific epitope of the soluble CD90 antigen is coated on the plate. It may also be possible to coat not only one but two, three or four or even more different monoclonal antibodies to the solid phase. The antibodies should be directed to different epitopes which are specific for epitopes of CD90.

When the test plates are used, the monoclonal antibodies attached to the solid phase are contacted with the sample derived from body fluid of the patient, preferably serum, and the CD90 antigen binds to the monoclonal antibody attached to the solid phase. After the usual washing steps the CD90 antigen attached to the monoclonal antibody (antibodies) bound to the solid phase are detected with another antibody directed against CD90 antigen. The second antibody which may generate a signal (e.g. colour, enzyme reaction) can be either a polyclonal serum against CD90 antigen or one or more other monoclonal antibodies directed to such epitopes of CD90 which do preferably not correspond with the epitopes to which the antibody attached to the solid phase is bound. Said second antibody is linked to a label or a suitable signal generating entity.

In another embodiment the present invention provides test kits which are specially adapted for performing the method described herein. The test kit comprises all means which are essential for performing the method of the present invention. Depending on the type of test used a test kit may comprise for example ELISA plates with a suitable antibody which binds specifically to soluble CD90. Furthermore, the test kit may comprise buffers or coloring agents. It is also possible that the test kit comprises another antibody which binds to another epitope of soluble CD90. This antibody may be directly or indirectly linked to a unit which generates a signal. It may for example be a dye or an enzyme which catalyzes a coloring reaction.

When the term "antibodies" is used in the present application this term comprises also antigen-binding portions of an antibody like Fab fragments, single chain antibodies and the like.

For the present method it is required to establish a calibration curve and to use negative and positive controls. According to the present method it is possible to detect soluble CD90 in body fluids. The value obtained is increased for certain forms of the disease. Therefore, it is required to establish a calibration curve by using defined amounts of CD90 antigen. If the amount of CD90 antigen calculated from the calibration curve is above a certain level it is an indication for certain risk factors for death occurring in particular in patients with SSc. The average values of sCD90 in serum are summarized in Table 1 below:

TABLE 1

| | ng/ml | preferred value in ng/ml |
|---|---|---|
| SSc without pulmonary complication | 300-340 | median 319 (interquartile range 303) |
| SSc with pulmonary fibrosis | 560-600 | median 576 (interquartile range 426) |
| SSc with pulmonary arterial hypertension | >680 | median 694 (interquartile range 494) |

In addition to the values measured ex vivo by the method according to the present invention it is of course required to take into account the clinical symptoms of the patient whose body fluid is used in the present invention. By taking into account the other clinical information obtainable from the patient it is possible to clearly decide for which further examination (e.g. right heart catheterization) the increased value of sCD90 is an indication.

In the method according to the present invention it is possible to detect the content of sCD90 in body fluids by using suitable antibodies which specifically bind to CD90. By using the calibration curve values can be calculated which correspond to the amount of sCD90 in the body fluid. The content of sCD90 is preferably measured in plasma or serum. Care has to be taken that the part of the body fluid which is measured is not treated by any step which changes the content of sCD90. Alternatively, it is also preferred to use as body fluid bronchoaveolar lavage fluids. According to the invention sCD90 is not measured in urine. In one embodiment of the present invention the content of sCD90 is measured in predetermined time intervals, which allows monitoring the progress and success of therapy.

According to the invention it is possible to identify among patients suffering from SSc those patients which show risk for a vascular and parenchymal involvement of the lung. Moreover, it is possible to conclude from the diagnostic method whether the patient suffers from pulmonary fibrosis and it is also possible to conclude from the values obtained by the diagnostic method whether the patient has an increased risk for PAH.

The results obtained by the method of the present invention can be used for selecting appropriate further diagnostics and therapy or in order to determine whether the disease of the patient is improved by applying the medication.

In the course of the present invention sCD90 serum concentrations were measured in a large cohort of SSc patients. In addition anthropometric, clinical, laboratory, and functional data in correlation to sCD90 levels in these patients were assessed.

As controls, sCD90 serum concentrations were measured in healthy volunteers and patients with idiopathic retroperitoneal fibrosis (IRF), a fibro-inflammatory disease, which is normally not affecting the lungs and the peripheral vasculature.

The tests were therefore performed with two groups of controls, namely healthy persons and patients suffering from a different disease.

Patients were recruited at the Department of Rheumatology and Clinical Immunology, University Medical Center Freiburg, Germany, and the Department of Rheumatology, University Hospital Basel, Switzerland. SSc patients fulfilled the criteria of the American College of Rheumatology (formerly, the American Rheumatism Association, Arthritis Rheum. (1980) pp. 581-590). Patients with clinical signs of acute infection were excluded. The diagnosis in patients with IRF was based on imaging and clinical findings. Patients with IRF due to known secondary causes were excluded.

Next to anthropometric and clinical data, bronchoalveolar lavage fluid (BALF) differentials and laboratory parameters were obtained. Skin score was measured by the modified Rodnan skin score (mRSS). Gas exchange at rest was assessed by the determination of hemoglobin-corrected single breath-diffusing capacity for carbon monoxide (DLCo)-Spirometry, bodyplethysmography and six-minute walk distance (6MWD) were measured according to established standards. PAH (systolic pulmonary arterial pressure (sPAP)≥40 mmHg in echocardiography) and pulmonary fibrosis (fibrotic changes on chest X-ray) were defined as proposed by the European League Against Rheumatism (EULAR) Scleroderma Trials and Research (EUSTAR) Group (Annals of the Rheumatic Diseases (2007) pp. 462-466). As controls the sera of healthy volunteers and patients with IRF were analyzed.

In a preferred embodiment enzyme-linked immunosorbent assay (ELISA) was performed as follows:

Nunc® microtiter plates were coated with 0.25 µg/well anti-Thy-1 (Thy-1 corresponds to CD90) antibody in 0.1 M $NaHPO_4$/0.1 M $NaH_2PO_4$ pH 9.0 (clone AS02; Dianova, Hamburg, Germany) overnight at 4° C. Plates were washed three times with PBS and blocked with PBS/10% FCS for 1 h at 4° C. After several washes with PBS, samples and standard (rhThy-1 expressed in CHO-cells) were diluted in PBS/10% FCS and incubated over night at 4° C. The plates were washed five times with PBS. The biotinylated anti-CD90 monoclonal antibody (clone 5E10, Pharmingen, Hamburg, Germany) was added for 90 min at 37° C. After three washes with PBS, avidin-conjugated peroxidase (eBioscience, Frankfurt, Germany) 1:10 000 diluted in assay diluent (eBioscience) was added for 1 h at room temperature. Plates were rinsed five times with PBS. Subsequently, tetramethylbenzidine was used to generate the colour reaction that was measured at 405 nm.

The values obtained were evaluated with acceptable statistical analysis methods.

All values are shown as medians and interquartile ranges (IQR). Subgroups were compared using the non-parametric Mann-Withney-U test and Fisher's exact test. For correlations Spearman's rank correlation coefficient was calculated. Multivariate logistic regression analysis was conducted to examine the influence of age, sex and sCD90 serum levels on PAH. Receiver operating characteristics (ROC) curves were calculated to analyse the value of sCD90 for diagnosing PAH and pulmonary fibrosis in SSc. Probability values below 0.05 were considered significant. SPSS (version 17, IBM Corp., New York, United States) and GraphPad Prism (GraphPad Software Inc., California, United States) were used for database management and statistical analysis.

The present invention shows that sCD90 serum concentrations are increased in patients with SSc compared to healthy control subjects and patients with IRF. Moreover, sCD90 levels are elevated in SSc patients with pulmonary involvement. Patients with pulmonary fibrosis and in particular PAH, revealed highly increased sCD90 serum concentrations.

Parenchymal and vascular pulmonary involvement are accounting for the majority of deaths in SSc. The pulmonary vasculature in patients with SSc could be affected by remodelling processes, which are preceded by EC activation and dysfunction.

Anti-EC-antibodies (AECA) may contribute to this process. AECA are elevated in the sera of patients with vascular manifestations of SSc such as digital ulcers or PAH, but also in idiopathic PAH.

In the development of PAH, activated EC's are proliferating and leading to vessel obstruction. Activated EC's are expressing several adhesion molecules. CD90 is a member of the immunoglobulin superfamily and as such, like other adhesion molecules, involved in cell-cell-adhesion and the recruitment of leukocytes via Mac-1 (CD11b/CD18).

It has been shown that CD90 is expressed by activated EC's. In mouse CD90 is expressed by T lymphocytes, which can shed the molecule spontaneously from their cell surface. Also other adhesion molecules can be released from the cell surface by enzymatic cleavage. The soluble adhesion molecules sVCAM-1, sE-selectin, and sICAM-1 are elevated in the sera of patients with SSc. There are some small studies regarding the association of these soluble adhesion molecules to disease severity and PAH in SSc: Denton and co-workers (Br. J. Rheumatol. 1995, p. 1048-1054) showed that changes of sVCAM-1 and sE-selectin concentrations paralleled decline of lung function and improvement of skin score and renal function in 6 out of 12 patients with SSc.

A study of 19 patients with SSc revealed that sVCAM-1 correlates with abnormal left ventricular filling patterns in echocardiography and the degree of dyspnoea. However, only two patients in this cohort had signs of PAH in echocardiography, and serum concentrations of sVCAM-1 and sICAM-1 in these two patients were not discussed. Moreover, in a study of 31 SSc patients it has been shown, that sVCAM-1 and sE-selectin are related to internal organ involvement of SSc (16 patients with internal organ involvement: 2 patients with PAH, 13 patients with pulmonary fibrosis and 1 patient with cardiac involvement).

Iannone et al. (Ann. Rheum. Dis. 2008, p. 1121-1126) showed that sICAM-1, sP-selectin, soluble platelet endothelial cell adhesion molecule-1 (sPECAM-1) and sVCAM-1 were elevated in 10 patients with SSc-PAH in comparison to healthy controls.

The present invention shows for the first time that sCD90 serum concentrations are elevated in patients with SSc and related to disease severity. In particular patients with PAH revealed high serum levels of this soluble adhesion molecule. Endothelin-1 (ET-1) expression is increased in patients with PAH and an important therapeutic target in this disease. ET-1 is linked to EC activation in patients with PAH and SSc and associated with serum levels of soluble adhesion molecules. Thus, it has been shown that sVCAM-1 and sICAM-1 serum levels were elevated in SSc-PAH and decreasing upon treatment with ET receptor blockers. These data are in accordance with the concept of EC activation and the present result showing highly elevated sCD90 levels in patients with SSc and PAH.

Another potential source of sCD90 in SSc might be fibroblasts. In fibroblast foci of patients with idiopathic pulmonary fibrosis only CD90− fibroblasts/myofibroblasts could be detected, whereas in healthy controls CD90+ fibroblasts predominate. In vitro stimulation of CD90+ fibroblasts with pro-fibrotic cytokines such as tumor-necrosis-factor-α and interleukin-1 leads to a shedding of CD90 from the cell surface and a differentiation towards a highly active myofibroblast phenotype. Presumably, CD90 is shed from the cell surface in course of such a differentiation process of fibroblasts, and thus causing increased serum concentrations of sCD90 in SSc patients.

In conclusion, sCD90 serum concentrations were elevated in patients with SSc, which is in accordance with the hypothesis of EC activation in SSc. In particular pulmonary fibrosis and, even more, PAH were associated with elevated sCD90 levels. The exact source of sCD90 has to be elucidated in further investigations. Moreover, the applicability of this soluble adhesion molecule for the diagnostic and monitoring purposes of PAH in SSc must be determined in further validation cohorts and prospective clinical trials.

In a preferred embodiment the present invention allows a diagnostic differentiation between patients with SSc from patients with PAH.

EXAMPLES

Results of the following experiments are summarized in the figures.

Example 1

Study Subjects

A total of 77 sera of patients with SSc (59 females; 18 males) referred between 2000 and 2011 were analysed. Since December 2010 data entry was performed prospectively. The clinical characteristics of the study population are shown in Table 2. The sera of 31 healthy volunteers (19 females; 12 males) and 29 patients with IRF (16 female; 13 male) served as controls. SSc patients did not significantly differ from patients with IRF and healthy controls with respect to age (p=0.7; p=0.15) and sex (p=0.05; p=0.16).

TABLE 2

Clinical characteristics of patients with systemic sclerosis

| Variable | Value |
| --- | --- |
| Subjects (N) | 77 |
| Active digital ulcers (yes/no) | 8/69 |
| mRSS | 6 (15) |
| Pulmonary fibrosis (yes/no) | 31/46 |
| PAH (yes/no) | 19/58 |
| sPAP (mmHg) | 29 (12) |
| NT-pro-BNP (pg/ml) | 103 (321) |
| TLC (% predicted) | 90 (27) |
| FVC (% predicted) | 89 (34) |
| $DL_{CO}$ (% predicted) | 65 (31) |
| 6MWD (m) | 433 (107) |
| BALF Macrophages (%) | 79.0 (27.5) |
| BALF Neutrophils (%) | 4.5 (9.0) |
| BALF Eosinophils (%) | 1.5 (4.3) |
| BALF Lymphocytes (%) | 7.0 (15.7) |

Data are shown as median values and interquartile ranges unless specified otherwise.
Definitions of abbreviations: mRSS = modified Rodnan Skin Score; PAH = pulmonary arterial hypertension; sPAP = echocardiographic systolic pulmonary arterial pressure; NT-pro-BNP = N-terminal pro-brain natriuretic peptide; TLC = total lung capacity; FVC = forced vital capacity; $DL_{CO}$ = single haemoglobin-corrected breath-diffusing capacity for carbon monoxide; 6MWD = six-minute walk distance; BALF = bronchoalveolar lavage fluid.

Example 2 sCD90 Serum Concentrations Are Elevated in SSc

Serum sCD90 concentrations were elevated in patients with SSc (470 (393) ng/ml) compared to healthy controls (258 (277) ng/ml; p=0.001) and patients with IRF (310 (254) ng/ml; p=0.01). There was no statistical significant difference between sCD90 levels of healthy volunteers and IRF patients (p=0.53) (FIG. 1).

Example 3 sCD90 Serum Concentrations and Clinical/Laboratory Data

Figure 2:
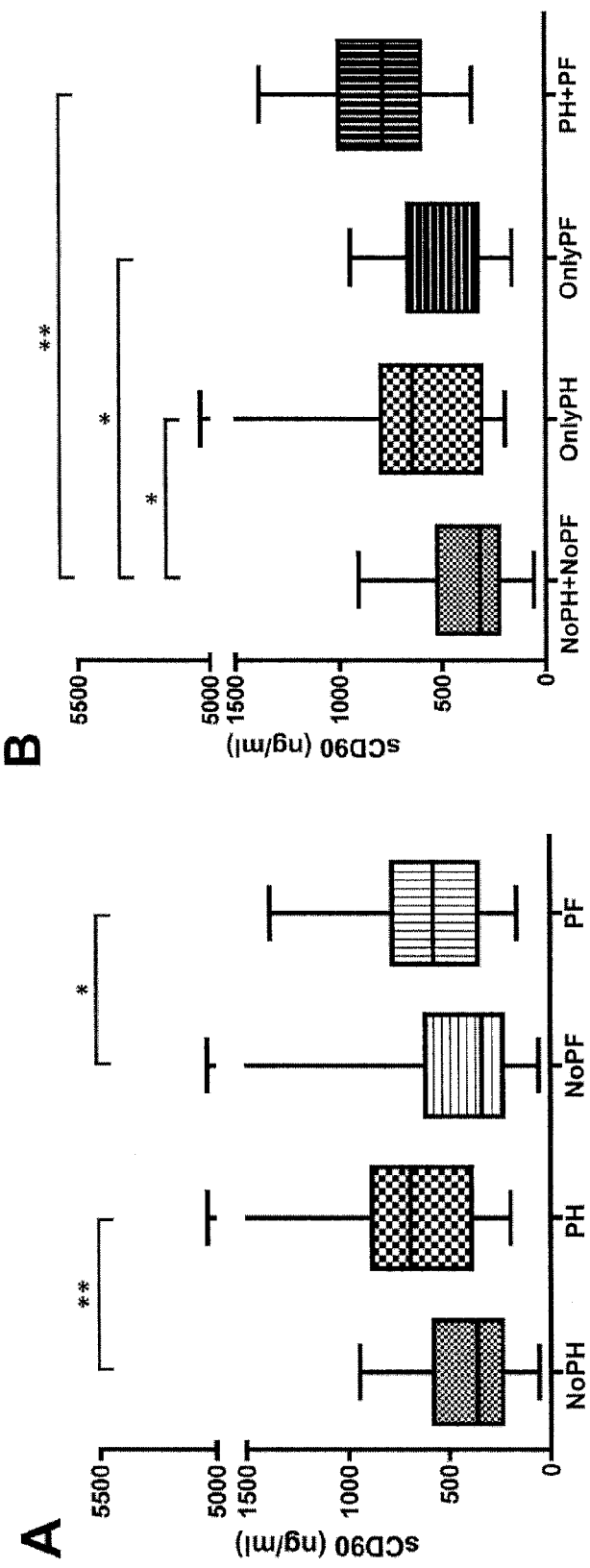
FIG. 2A and 2B. Soluble CD90 (sCD90) serum concentrations of patients (in ng/ml) with systemic sclerosis and pulmonary involvement. *=p<0.05; **=p<0.005. Definitions of abbreviations: PH=pulmonary arterial hypertension; PF=pulmonary fibrosis.

SSc patients with pulmonary fibrosis (n=31) revealed significantly higher serum concentrations of sCD90 than SSc patients without pulmonary fibrosis (576 (426) vs. 337 (382) ng/ml; p=0.006). There was a significant difference of sCD90 serum concentrations between patients with PAH (n=19) and those without PAH (694 (494) vs. 361 (338) ng/ml; p<0.001) (FIG. 2A).

Example 4

Patients with PAH and pulmonary fibrosis (n=9) showed highly increased sCD90 levels compared to patients having neither PAH nor pulmonary fibrosis (787 (399) vs. 319 (303) ng/ml; p<0.001). sCD90 levels in patients with isolated PAH (n=10) were significantly elevated in comparison to patients without PAH and pulmonary fibrosis (647 (464) vs. 319 (303) ng/ml; p=0.02). Patients with isolated pulmonary fibrosis (n=22) revealed significantly increased sCD90 levels compared to patients without PAH and pulmonary fibrosis (502 (331) vs. 319 (303) ng/ml; p=0.026) (FIG. 2B).

Between SSc patients with and those without pulmonary fibrosis there was no significant difference regarding age (p=0.21), whereas patients with PAH were significantly older (p<0.001). Multivariate logistic regression analysis of age, sex, sCD90 and pulmonary fibrosis revealed that age and sCD90 serum concentrations were associated with PAH, whereas sex and pulmonary fibrosis were not (Table 3).

TABLE 3

Multivariate logistic regression analysis for pulmonary arterial hypertension

| Variable | Odds ratio (95% CI) | p-value |
| --- | --- | --- |
| Age | 1.101 (1.030-1.177) | 0.003 |
| Sex | 0.320 (0.072-1.416) | 0.133 |
| Soluble CD90 | 1.004 (1.001-1.006) | 0.016 |
| Pulmonary fibrosis | 0.696 (0.176-2.752) | 0.476 |

Definitions of abbreviations: CI = confidence interval.

Moreover, sPAP significantly correlated with sCD90 serum concentrations (n=54; r=0.470; p<0.001). A correlation between serum concentrations of N-terminal pro-brain natriuretic peptide (NT-proBNP) and sCD90 marginally failed statistical significance, most likely due to many missing data points (n=27; r=0.338; p=0.08). Forced vital capacity (n=64; r=−0.144; p=0.26) and total lung capacity (n=67; r=−0.230; p=0.06) did not correlate with sCD90 levels, whereas there was a significant correlation between $DL_{CO}$ and sCD90 (n=66; r=−0.349; p=0.004). A correlation between 6MWD and sCD90 was not observed (n=22; r=−0.189; p=0.4). With regard to the cellularity of the BALF, there was no significant correlation between sCD90 levels and the percentage of lymphocytes (n=18, r=0.082; p=0.747), macrophages (r=0.095; p=0.708), neutrophils (r=0.042; p=0.867), and eosinophils (r=0.045; p=0.858). Active digital ulcers (n=8) were also not associated with higher sCD90 serum levels (491 (345) vs. 407 (392) ng/ml; p=0.96). A correlation between sCD90 and skin fibrosis assessed using the modified Rodnan Skin Score (n=67; r=0.250; p=0.04) has been found.

Example 5 sCD90 and Pulmonary Involvement

Figure 3:
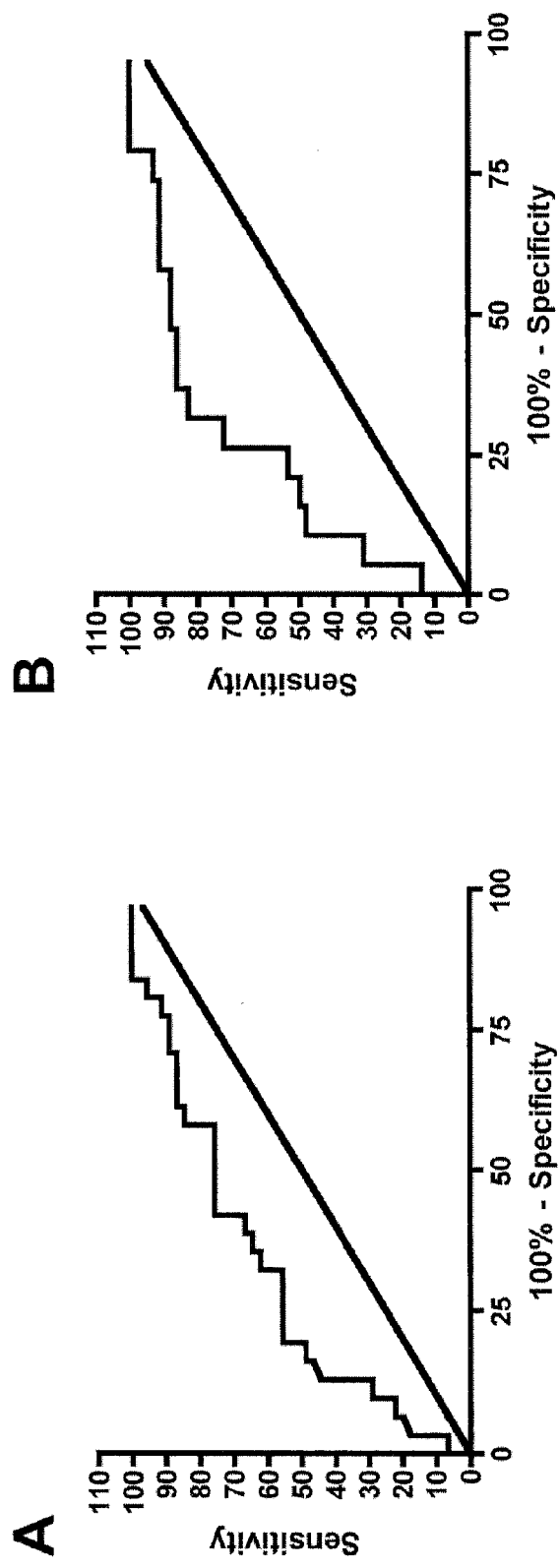
FIG. 3A: Receiver operating characteristics (ROC) curves. A cut-off value of ≥456 ng/ml sCD90 serum concentration had a sensitivity of 68% and a specificity of 61% for pulmonary fibrosis in SSc (area under the curve 0.685; 95% CI: 0.565-0.806; p=0.006; positive likelihood ratio: 1.7).
FIG. 3B: For pulmonary arterial hypertension sCD90 serum concentrations ≥626 ng/ml revealed a sensitivity of 68% and a specificity of 83% (area under the curve 0.772; 95% CI: 0.646-0.898; p<0.001; positive likelihood ratio: 4.0).

To address the diagnostic value of sCD90 for the occurrence of PAH and pulmonary fibrosis in SSc ROC curves were calculated. For pulmonary fibrosis in SSc sCD90 concentrations ≥456 ng/ml showed a sensitivity of 68% and a specificity of 61% (area under the curve 0.685; 95% CI: 0.565-0.806; p=0.006). A cut-off value of ≥626 ng/ml revealed a sensitivity of 68% and a specificity of 83% for PAH (area under the curve 0.772; 95% CI: 0.646-0.898; p<0.001) (FIG. 3). Interestingly, all patients with sCD90 serum concentrations ≥1000 ng/ml revealed PAH (3 patients).

The invention claimed is:
1. A method for the diagnosis, treatment and optional/therapeutic monitoring of systemic sclerosis in a patient in need thereof, said method comprising the steps of:
   (a) detecting and measuring the concentration of soluble CD90 in a body fluid sample obtained from said patient, wherein said body fluid sample is selected from the group consisting of serum, plasma and bronchoalveolar lavage fluid;
   (b) comparing the concentration of soluble CD90 measured in step (a) to a reference level of soluble CD90 associated with a healthy subject or a subject with idiopathic retroperitoneal fibrosis;
   (c) diagnosing the patient with pulmonary fibrosis and/or pulmonary arterial hypertension when the comparison of step (b) reveals that the concentration of soluble CD90 in said body fluid sample is elevated relative to said reference level;
   (d) administering a treatment specific for pulmonary arterial hypertension to the patient diagnosed with pulmonary fibrosis and/or pulmonary arterial hypertension in step (c), wherein said treatment specific for pulmonary arterial hypertension comprises the administration of one or more Endothelin-1 receptor blockers; and
   (e) optionally monitoring the progress of the treatment of step (d) by repeating steps (a) and (b) at predetermined time intervals, wherein a decrease over time in the concentration of soluble CD90 in subsequent body fluid sample(s) is indicative of successful therapy.

2. The method according to claim 1, further comprising the step of differentiating between vascular and parenchymal involvement of a lung in said patient based on the concentration of soluble CD90 measured in said body fluid sample obtained from said patient in accordance with claim 1, wherein an elevated concentration of soluble CD90 in said body fluid sample as compared to said reference level is indicative of parenchymal involvement of a lung.

3. The method according to claim 1, further comprising the step of distinguishing a diagnosis of systemic sclerosis with pulmonary fibrosis from a diagnosis of systemic sclerosis without pulmonary fibrosis based on the concentration of soluble CD90 measured in said body fluid sample obtained from said patient in accordance with claim 1, wherein an elevated concentration of soluble CD90 in said body fluid sample as compared to said reference level is indicative of a diagnosis of systemic sclerosis with pulmonary fibrosis in said patient.

4. The method according to claim 1, further comprising the step of diagnosing said patient with pulmonary arterial hypertension based on the concentration of soluble CD90 measured in said body fluid sample obtained from said patient in accordance with claim 1, wherein an elevated concentration of soluble CD90 in said body fluid sample as compared to said reference level is indicative of a diagnosis of pulmonary arterial hypertension in said patient.

5. The method according to claim 1, further comprising the step of differentiating a diagnosis of pulmonary arterial hypertension from a diagnosis of systemic sclerosis based on the concentration of soluble CD90 measured in said body fluid sample obtained from said patient in accordance with in claim 1, wherein an elevated concentration of soluble CD90 in said body fluid sample as compared to said reference level is indicative of a diagnosis of systemic sclerosis patients with pulmonary arterial hypertension.

6. The method according to claim 1, wherein the concentration of soluble CD90 is measured by immunological methods.

7. The method according to claim 1, wherein the concentration of soluble CD90 is measured by an ELISA method.

8. The method according to claim 1, wherein the concentration of soluble CD90 in the sample is measured with a calibration curve.

9. A method for the diagnosis and/treatment of diffuse systemic sclerosis in a patient in need thereof, said method comprising the steps of:
   (a) obtaining a body fluid sample from said patient, wherein said body fluid sample is selected from the group consisting of serum, plasma and bronchoalveolar lavage fluid;
   (b) contacting said body fluid sample with an antibody specific for soluble CD90 so as to generate an antibody-CD90 complex;
   (c) detecting the presence and measuring the amount of the antibody-CD90 complex generated in step (b);
   (d) calculating the concentration of soluble CD90 in said body fluid sample based on the measurement obtained in step (c);
   (e) comparing the concentration of soluble CD90calculated in step (d) to a reference level of soluble CD90 associated with a healthy subject or a subject with idiopathic retroperitoneal fibrosis;
   (f) diagnosing the patient with pulmonary fibrosis and/or pulmonary arterial hypertension when the comparison of step (e) reveals that the concentration of soluble CD90 in said body fluid sample is elevated relative to said reference level; and
   (g) administering a treatment specific for pulmonary arterial hypertension to the patient diagnosed in step (d), wherein said treatment specific for pulmonary arterial hypertension comprises the administration of one or more Endothelin-1 receptor blockers.

10. The method according to claim 9, further comprising the step of monitoring the progress of the treatment of step (d) by repeating steps (a) - (e) at predetermined time intervals, wherein a decrease over time in the concentration of soluble CD90 in said body fluid sample(s) is indicative of successful therapy.

* * * * *